United States Patent
Liu

(10) Patent No.: US 8,259,897 B2
(45) Date of Patent: Sep. 4, 2012

(54) COMPUTED TOMOGRAPHY METHOD AND APPARATUS FOR CENTRE-OF-ROTATION DETERMINATION

(75) Inventor: Tong Liu, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 12/989,170

(22) PCT Filed: Apr. 25, 2008

(86) PCT No.: PCT/SG2008/000140
§ 371 (c)(1),
(2), (4) Date: Dec. 9, 2010

(87) PCT Pub. No.: WO2009/131544
PCT Pub. Date: Oct. 29, 2009

(65) Prior Publication Data
US 2011/0103545 A1 May 5, 2011

(51) Int. Cl.
*A61B 6/00* (2006.01)
*G01D 18/00* (2006.01)
(52) U.S. Cl. .......................... 378/4; 378/207
(58) Field of Classification Search .............. 378/4, 207
See application file for complete search history.

(56) References Cited

U.S. PATENT DOCUMENTS

| | | | | |
|---|---|---|---|---|
| 4,812,983 | A | * | 3/1989 | Gullberg et al. ............... 378/14 |
| 5,214,578 | A | * | 5/1993 | Cornuejols et al. .......... 378/207 |
| 2005/0276375 | A1 | * | 12/2005 | Urushiya ....................... 378/19 |
| 2007/0274456 | A1 | * | 11/2007 | Holt .............................. 378/207 |
| 2008/0253510 | A1 | * | 10/2008 | Liu ................................ 378/19 |

FOREIGN PATENT DOCUMENTS

| | | |
|---|---|---|
| JP | 2004-37267 | 2/2004 |
| WO | PCT/SG2005/000354 | 4/2007 |

* cited by examiner

*Primary Examiner* — Alexander H Taningco
(74) *Attorney, Agent, or Firm* — Altera Law Group, LLC

(57) ABSTRACT

A method and apparatus is disclosed for determining the central ray of scanning an object on a detector in a computer tomography system. The method comprises producing a fan beam of x-rays at a fixed x-ray source and detecting the x-rays at the detector. The scanning projection data of the object under examination is received and the object is rotated under examination using a manipulator. After calculating the opposite projection pixel position and projection angle for each pixel, a mismatching is measured between the grey levels of all pixels and their calculated opposite projection pixels with a set of assumed central ray, and identifying the minimum of the measurement as the true central ray.

19 Claims, 20 Drawing Sheets

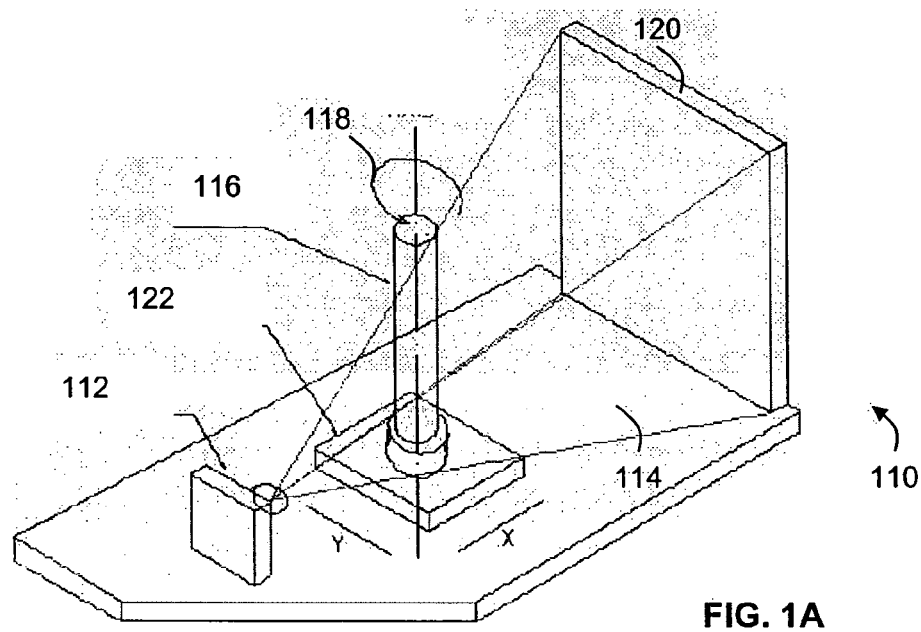
FIG. 1A
FIG. 1B
| | Lookup table | |
|---|---|---|
| Y | Z | Central Ray |
| Y1 | Z1, Z2, ..., Zn | C1 |
| Y2 | Z1, Z2, ..., Zn | C2 |
| ... | ... | ... |
| Yn | Z1, Z2, ..., Zn | Cn |
140
FIG. 2

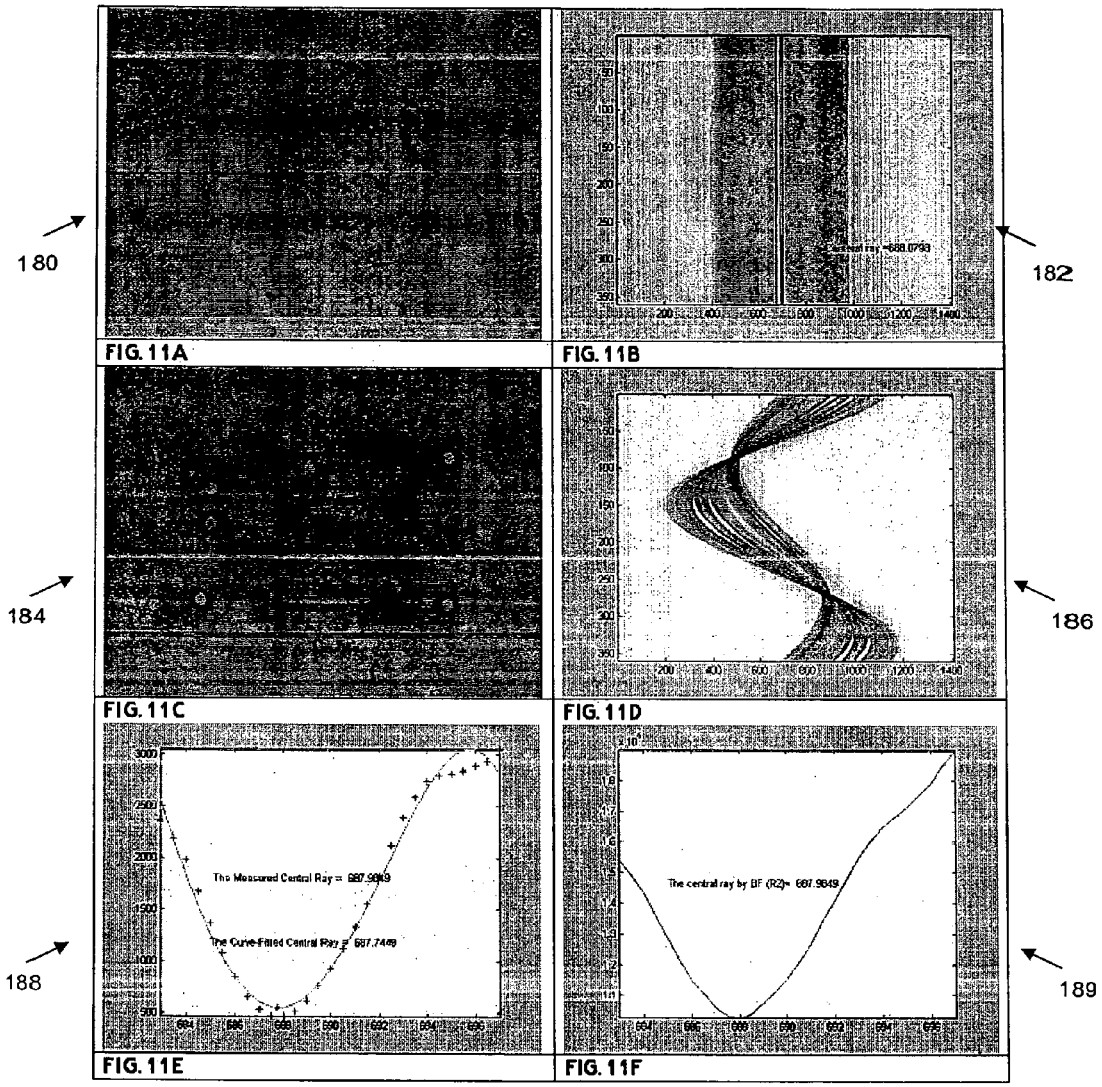

| Image Size | Processing Time (seconds) | | Result of the fine search round | |
|---|---|---|---|---|
| | Universal Method | Embodiment | Universal Method | Embodiment |
| 700 x 700 | 2580 | 90 | | |
| 470 x 470 | 1260 | 50 | | |
| 350 x 350 | 740 | 30 | | |
| 200x200 | 480 | 20 | | |

FIG. 12

FIG. 17A FIG. 17B
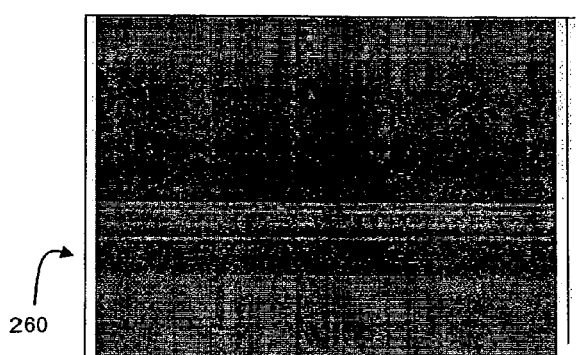
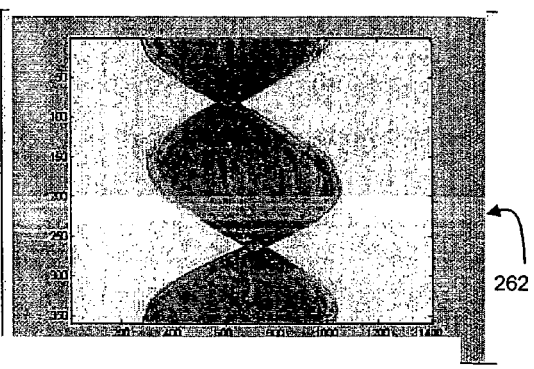
FIG. 17C FIG. 17D
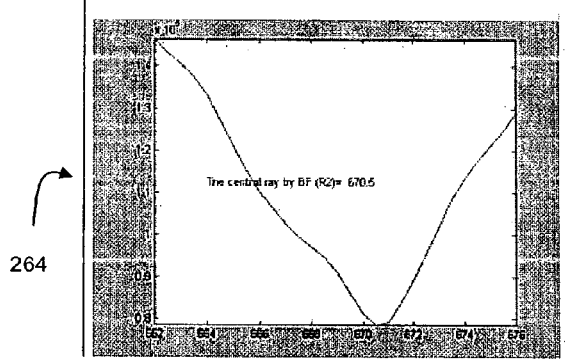
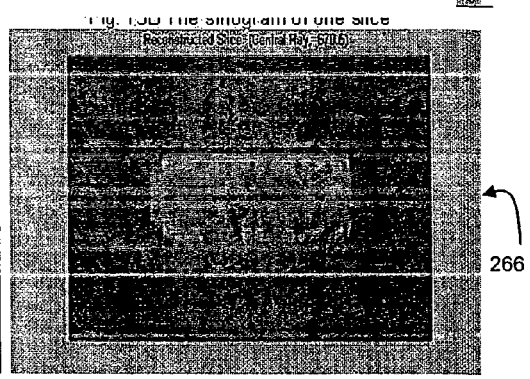

COMPUTED TOMOGRAPHY METHOD AND APPARATUS FOR CENTRE-OF-ROTATION DETERMINATION

FIELD OF THE INVENTION

This invention relates to an automated method and algorithm for fast determination of the axis of rotation in a computed tomography (CT) scanning independent of the practical scanning manner and the object position. More specifically, a centre of rotation is determined with the scanning projections of the examination object without any prior calibration with a minimized processing time and suitable accuracy.

BACKGROUND OF THE INVENTION

The central ray in CT scanning systems is the projection of the centre-of-rotation on the detector. The central ray must be a known parameter for all reconstruction algorithms. Any error in the central ray generally leads to artifacts and distortion in the reconstructed images which sometimes are very difficult to identify. The current conventional methods used for central ray determination are discussed.

A conventional method is by using a fixed position. Like many medical check X-ray CT, the centre of rotation is always fixed and usually only needs to be calibrated once a year, for example. For this system, because a resolution of about several millimeters is acceptable, there is no high accuracy requirement about the central ray. The use of a fixed centre of rotation is only applicable to medical X-ray CT system because micro-CT systems for industry applications typically need to adjust the magnification and scanning position of the object according to the size, shape of the object and the requirement for different resolution.

FIG. 1A illustrates a conventional system 110 for determining central ray utilizing a wire phantom 116. FIG. 1A illustrates a conventional method of a wire phantom that is scanned first to generate a sinogram of the wire from which the central ray can be determined. A wire phantom is actually a small straight wire fixed at the centre of a plastic tube. The wire is made of heavy metal such as tungsten. It must be small enough so that it can be treated as a point to meet the requirement for certain accuracy. With the wire phantom method, before scanning the object, the wire phantom is scanned first for a whole round at the same place used for scanning the object. The sinogram of the projection data of the wire phantom is used to determine the central ray. In the system 110, a source 112 is projecting a projection beam 114 towards the wire phantom 116 and detected by a digital detector 120. A manipulator and rotator 122 rotate the wire phantom about a rotation of axis 118. FIG. 1A illustrates the situation where a wire phantom is scanned and FIG. 1B is a typical sinogram 130 of this scan. Calibration with a wire phantom is currently a common practice in many existing commercially available systems. However, this method requires one more scanning which greatly slows down the whole inspection process and reduces the effective lifetime of the system for real applications. It also presents significant calibration error in high-magnification scanning due to the mechanical movement involved.

FIG. 2 illustrates another conventional approach that uses a look-up table 140. A look-up table is actually a relationship between the central ray and the scanning position. It is usually established by scanning a calibration unit such as a wire phantom with the rotation axis placed at different positions. Once a lookup table is created, the central ray in a particular scan is read from the look up table according to the actual object position. Using a lookup table is straightforward but in practice this is simply not reliable because of the high requirement for the accuracy and repeatability of the manipulation system. Considering the large area of movement and multiple movement degrees of freedom, the look up table approach is only used for low-accuracy or low-resolution inspection applications. For some micro-CT system for industry applications, a lookup table about the relationship between the central ray and the scanning physical position is pre-calibrated and created.

FIG. 3A illustrates another conventional approach 150 using a geometrical relationship of the scanning. This method makes use of the property that during the scanning the boundary of the sinogram is generated always by the point that has the longest distance to the centre of rotation. With the knowledge of the central channel 162, the central ray 164 may be unambiguously determined from the left and right boundary points 158,160, in accordance with relationship between the object rotation axis 152 and the two tangential points 154, 156. FIG. 3B shows a sinogram and boundary detection 170 obtained with this method. The geometrical method has been proven to be an effective method which eliminates the need for extra scan and is able to provide a comparable accuracy to other methods such as calibrating with a wire phantom. However, this method generally only works with a normal scan which requires an object to be fully covered in the X-ray fan beam. Besides, this method encounters a certain difficulty if large fluctuation in X-ray intensity occurs during the scanning process or poor image contrast is observed around the two boundary points.

In a conventional method such as the universal method as shown in FIG. 4A-C, a flowchart (FIG. 4A) and graphs (FIGS. 4B and 4C) of a conventional method is shown for determining the central ray by measuring the mismatching level of two CT images reconstructed for one slice respectively with part of the projection data. FIG. 4A shows a typical flow chart of this method with a two-step strategy, that is, a rough search round with a large search range and a large search step followed by a fine search round with a small search range and a small search step. This method performs two reconstructions for one slice respectively with 1-180 views and 181-360 views over a set of assumed central ray values and measures the mismatching level of the two reconstructed images for each assumed central ray. The central ray value that corresponds to the minimum of the measurement in the fine search round will be determined as the best estimate to the real central ray. FIG. 4B and FIG. 4C show respectively the typical search results 54,56 in the rough search round and the fine search round. A slice is first reconstructed with half of the projections (1-180 views), then reconstructed with another half of the projections (181-360 views) over a set of assumed central rays, measuring the mismatching level of the two reconstructed images by performing an subtraction-square-sum operation between them, and identifying the real central ray as the one corresponding to the minimum of the measurement. This method is an automated method that does not require any prior calibration for scanning an object at any positions within the X-ray beam. The universal method has an accuracy at least as good as the wire phantom method, much better than the lookup table method, and more reliable and robust than the geometrical method which relies on the accurate detection of the boundary information of the sinogram. The main problem of the universal central ray method is that it is still thought as too slow for future in-situ application or high-throughput inspection. The universal method involves iterative reconstructions of one slice over a set of assumed central ray values within a search range defined 38. With each assumed central ray in the search range, the sinogram needs to go through the processes of the fan-beam to parallel-beam conversion 38, forward and Inverse Fourier transform 39, and two reconstructions, one with 1-180 views 40 and one with 181-360 views 42. The determination time is mainly determined by the reconstruction size, the step size and the search range defined. Among all the processes, the Fourier transform and the reconstruction 44 take about more than 90% of the total time required. For example, if a two-step search strategy is used, which typically involves about 40 cycles, a program written in Matlab would take about 20 minutes to complete the whole process with a reconstruction size of 200×200. A two-step strategy means one rough search 46 with a large search range and a large search step size is followed by a fine search 48 with a small search range and a small step size. If using a program written in C++, this may reduce to about 4 minutes.

There is thus a need for a system and method that alleviates the problems associated with the above universal central ray determination procedures. There is a need for an automated and fast method and algorithm that can directly determine the central ray with the fan-beam projection data of the object to be scanned. There is a need for a reliable and robust central ray determination method which is insensitive to intensity variation of the X-ray. There is a need for a measurement method for the quality of the reconstructed images in computed tomography (CT).

SUMMARY

An aspect of the invention is a method for determining the central ray of scanning an object on a detector in a computer tomography system, the method comprising:
producing a beam of x-rays at a fixed x-ray source; detecting the x-rays at the detector;
receiving scanning projection data comprising a plurality of pixels of the object under examination; rotating the object under examination using a manipulator;
selecting a first projection pixel position from the projection data, calculating a second projection pixel position, a gray level, and a projection angle for each pixel;
measuring the mismatching of gray levels of pixels and their corresponding second projection pixels with a set of predetermined central rays; and
identifying the minimum of the measurements as the estimate of the true central ray value.

An aspect of the invention is a computed tomography system for determining the central ray of scanning an object, the system comprising a fixed x-ray source for producing a beam; a digital detector for detecting the x-ray projection, a manipulator for holding and rotating an object under examination in the fan beam; and a processor receiving scanning projection data comprising a plurality of pixels of the object under examination from the digital detector; and the processor comprising a module for selecting a first projection pixel position from the projection data; calculating a second projection pixel position, a gray level, and a projection angle for each pixel; measuring the mismatching of gray levels of pixels and their corresponding second projection pixels with a set of predetermined central rays; and identifying the minimum of the measurements as the estimate of the true central ray value.

An aspect of the invention is a computer program product comprising a computer readable medium having computer program code means which, when loaded on a computer, makes the computer perform a method for determining the central ray of scanning an object under examination on a detector in a computer tomography system, the method comprising providing scanning projection data comprising a plurality of pixels of the object under examination produced by rotating the object under examination using a manipulator in a beam of x-rays from a fixed x-ray source and detecting x-rays at the detector; selecting a first projection pixel position from the projection data, calculating a second projection pixel position, a gray level, and a projection angle for each pixel; measuring the mismatching of gray levels of pixels and their corresponding second projection pixels with a set of predetermined central rays; and identifying the minimum of the measurements as the estimate of the true central ray value.

BRIEF DESCRIPTION OF THE DRAWINGS

In order that embodiments of the invention may be fully and more clearly understood by way of non-limitative example from the following description taken in conjunction with the accompanying drawings in which like reference numerals designate similar or corresponding elements, regions and portions, and in which:

FIG. 1A-B is a schematic drawing of a conventional system using a wire phantom and a sinogram of the projection data of the wire phantom used to determine the central ray, respectively;

FIG. 2 is a schematic drawing of a conventional system using a lookup table;

FIG. 11A-F shows the comparison for accuracy between the wire phantom method (FIG. 11A-B), the universal method (FIG. 11C-E) and an embodiment of the invention (FIG. 11F);

FIG. 12 shows a table of comparison for processing time between the conventional automated universal method and an embodiment of the invention;

FIG. 17A-D demonstrates the performance of an embodiment of the invention of a normal scan with a six-layer sample;

DETAILED DESCRIPTION

Figure 3A:
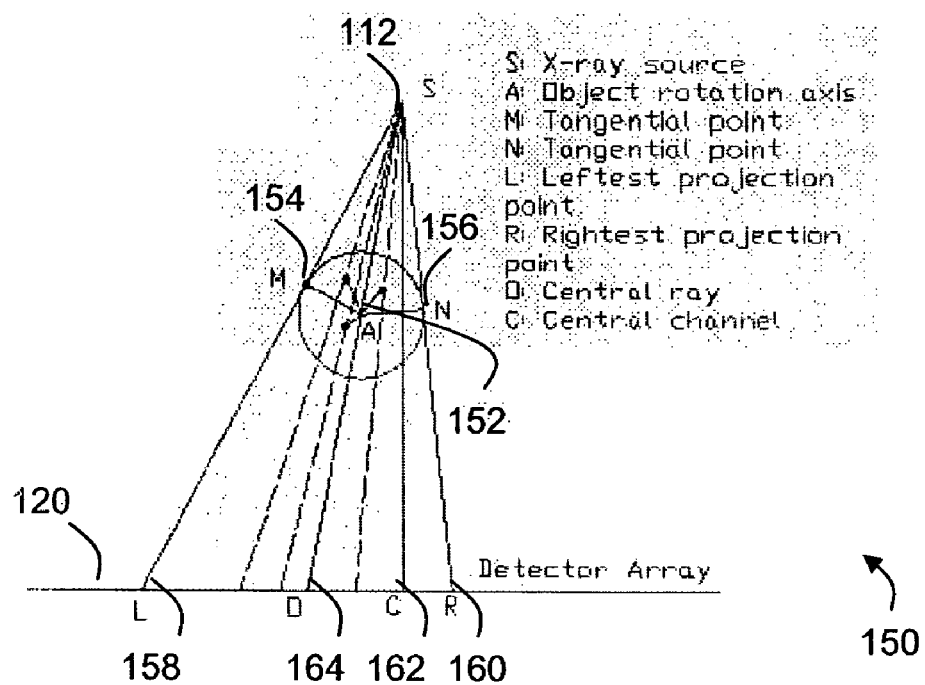
FIG. 3A-B is a schematic drawing of a conventional system using a geometrical method and sinogram and boundary detection, respectively.
Figure 3B:
Figure 4A:
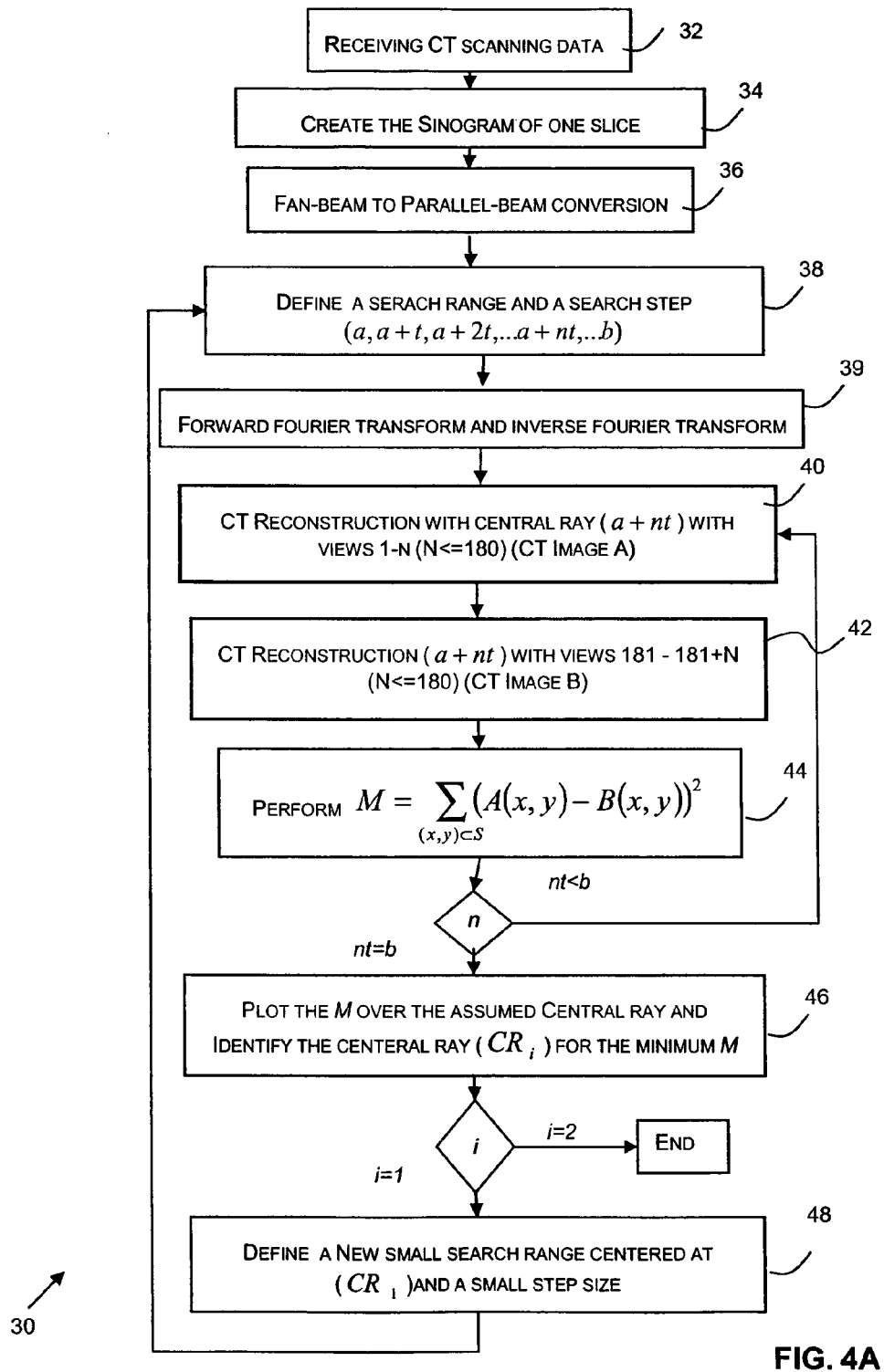
FIG. 4A-C shows a flowchart (FIG. 4A) and graphs (FIGS. 4B and 4C) of a conventional method for determining the central ray by measuring the mismatching level of two CT images reconstructed for one slice respectively with part of the projection data.
Figure 4B:
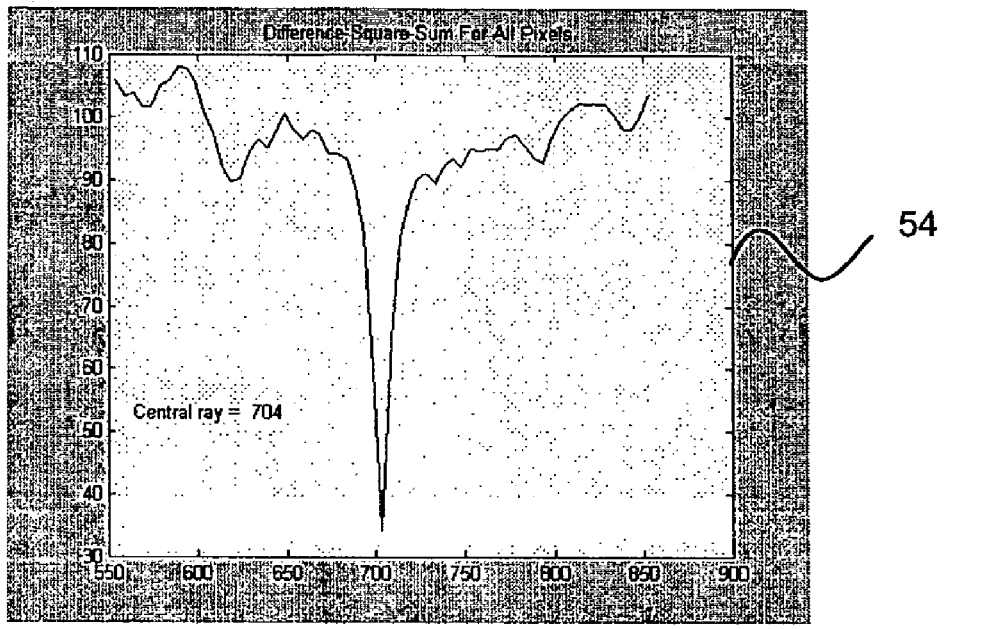
Figure 4C:
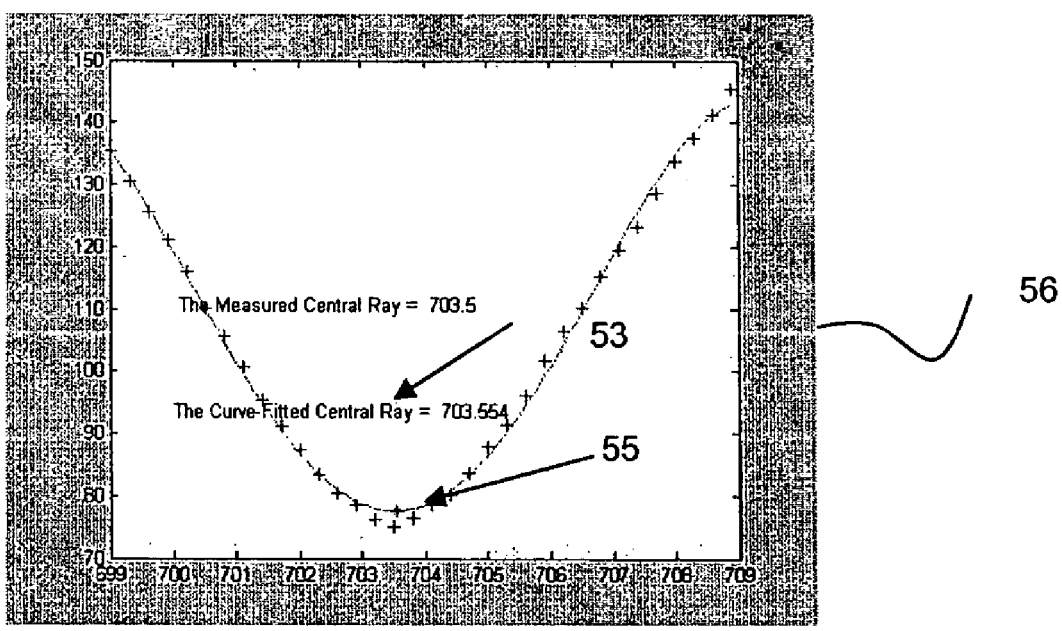
Figure 5:
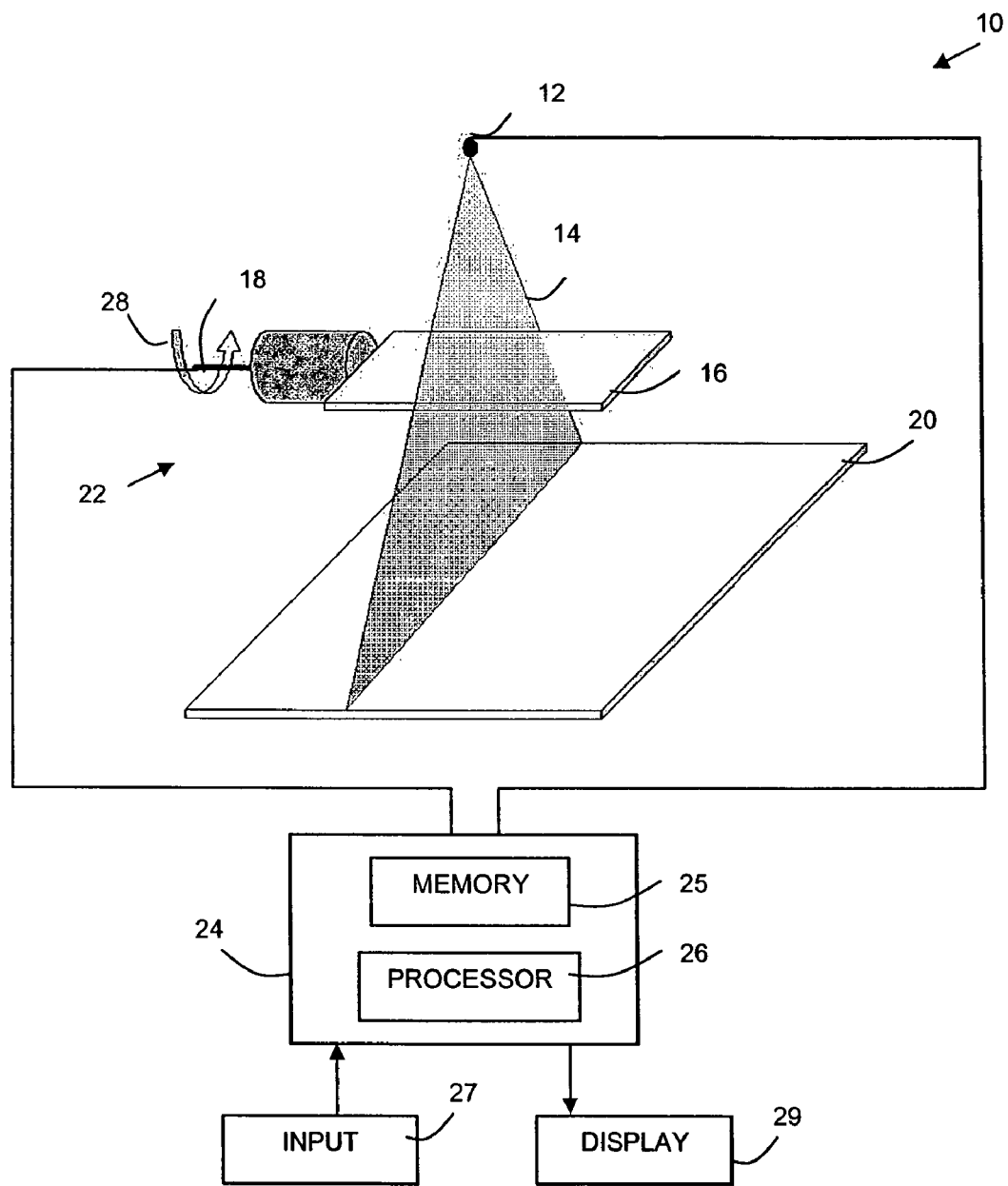
FIG. 5 is a schematic diagram of a CT scanning system in accordance with an embodiment of the invention.

FIG. 5 illustrates a schematic diagram of a CT scanning system in accordance with an embodiment of the invention. FIG. 5 shows the general concept of a CT system which comprises of a source 12, a DDD detector 20, a rotary unit 22 and an examination subject 16, for example an integrated circuit (IC) chip. The system further comprises a processing system 24 having a processor 26, a memory 25, and input 27 and display 29 for displaying the projections and reconstructed images. The rotary unit 22 can rotate the subject around a rotation axis 18 in a rotation direction 28 to generate multiple projections for various angles which then are used for CT reconstruction. The system and method in accordance with an embodiment of the invention is for determining the central ray, i.e. the projection of the centre of rotation on the detector, with the scanning projection data of the object under examination by measuring the mismatching level of two sub-sinograms after the fan-beam to parallel-beam conversion with a set of assumed central ray.

Figure 6A:
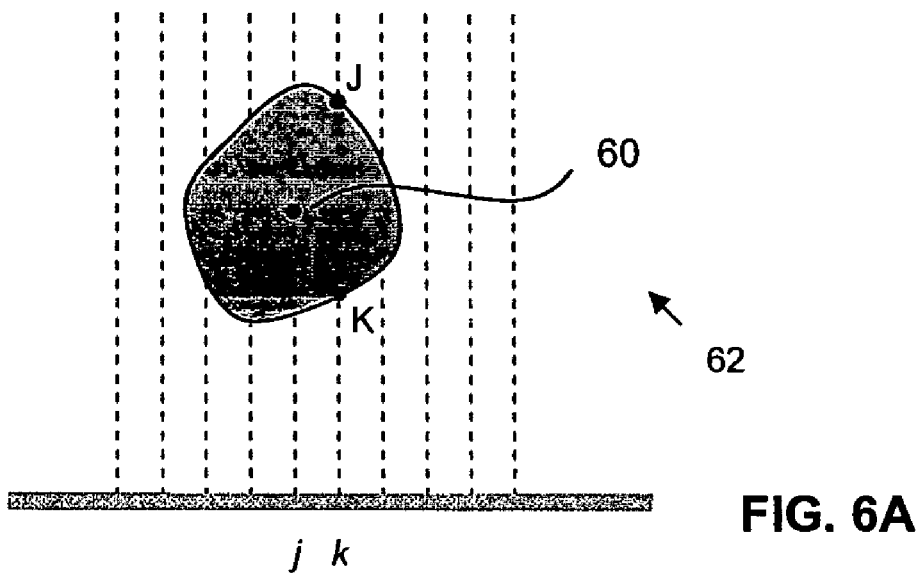
FIG. 6A-B illustrate the principle of an embodiment of the invention with a parallel-beam system configuration with a projection at angle α and at angle α+180°.
Figure 6B:
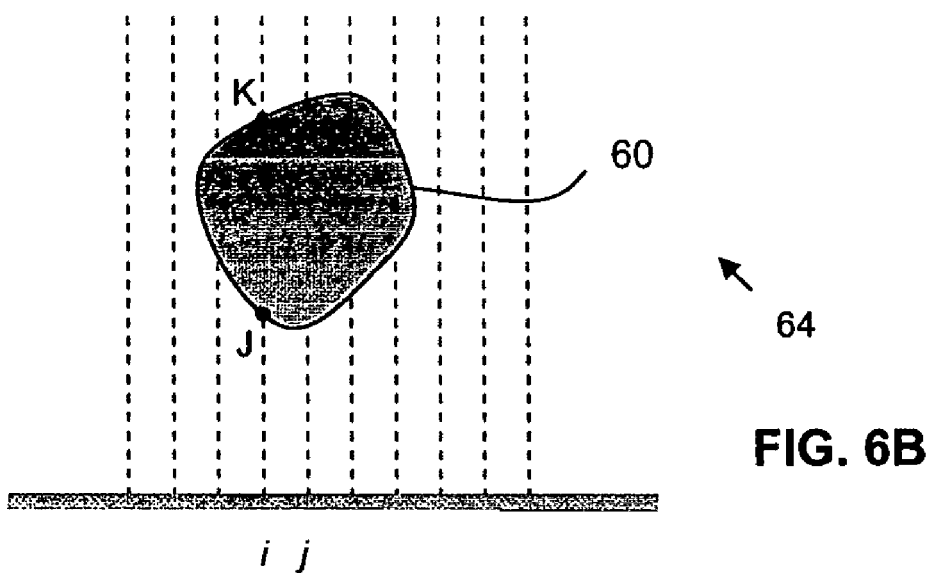

FIG. 6A-B illustrates the principle of an embodiment of the invention with a parallel-beam inspection configuration. FIG. 6A shows a projection at an angle of α 62. The projection of the centre-of-rotation 60 on the detector is the pixel number j and the path J-K is projected on the detector at pixel number k. If the sample is rotated 180 degree 64 as shown in FIG. 6B, the central ray is still at pixel number j. However, the projection of path J-K (now K-J) is at pixel number i. It may be obtained that (k−j)=(j−i). If it is supposed that the detector size is m (m is an odd integer); the central ray is at (m−1)/2+1 that is the centre of the projection; and the two projections captured at angle α and α+180 respectively are $P_\alpha$ and $P_{\alpha+180}$. Ideally this should be $$P_\alpha(i) = P_{\alpha+180}(m+-i-1) \qquad (1)$$

i is the $i^{th}$ pixel in the projection vector.

If a flip around the centre of the projection ((m−1)/2+1) is performed, that is $$P^{(f)}_\alpha(i) = P_{\alpha+180}(m-i+1) \qquad (2)$$

then ideally, without consider the noise issue, yields $$P_\alpha(i) = P^{(f)}_{\alpha+180}(i) \qquad (3)$$

However, if real central ray is not at the centre of the projection ((m−1)/2+1), the above flipping operation will generate a resultant $P^{(f)}_{\alpha+180}$ that would have a certain shifting to the projection $P_\alpha(i)$. Then equation (3) is no long valid. The larger the error to the real central ray, the larger the mismatching level between $P_\alpha(i)$ and $P^{(f)}_{\alpha+180}$. Therefore by performing the following operation $$\text{Measurement} = \sum_{i=1}^{m} \left(P_\alpha(i) - P^{(f)}_{\alpha+180}(i)\right)^2 \qquad (4)$$

the measurement of the mismatching level over a central ray value that assumed at ((m−1)2+1) is obtained.

With a 360 degree scanning with a 1-degree angular internal, the mismatching level may be measured using the projections from 1 to 180 (sub-sinogram A) and those projections from 181 to 360 (sub-sinogram B) by performing $$C(x, y) = B(x, m - y + 1) \qquad (5)$$

$$\text{Measurement} = \sum_{((x,y) \subset s, s \leq S)} (A(x, y) - C(x, y))^2 \qquad (6)$$

where (x,y) is the row number and the column number in B and C, and S is an area that is less than or equal to A and B; repeating the above process over a set of central ray values using either a one-step or two-step strategy.

Figure 7:
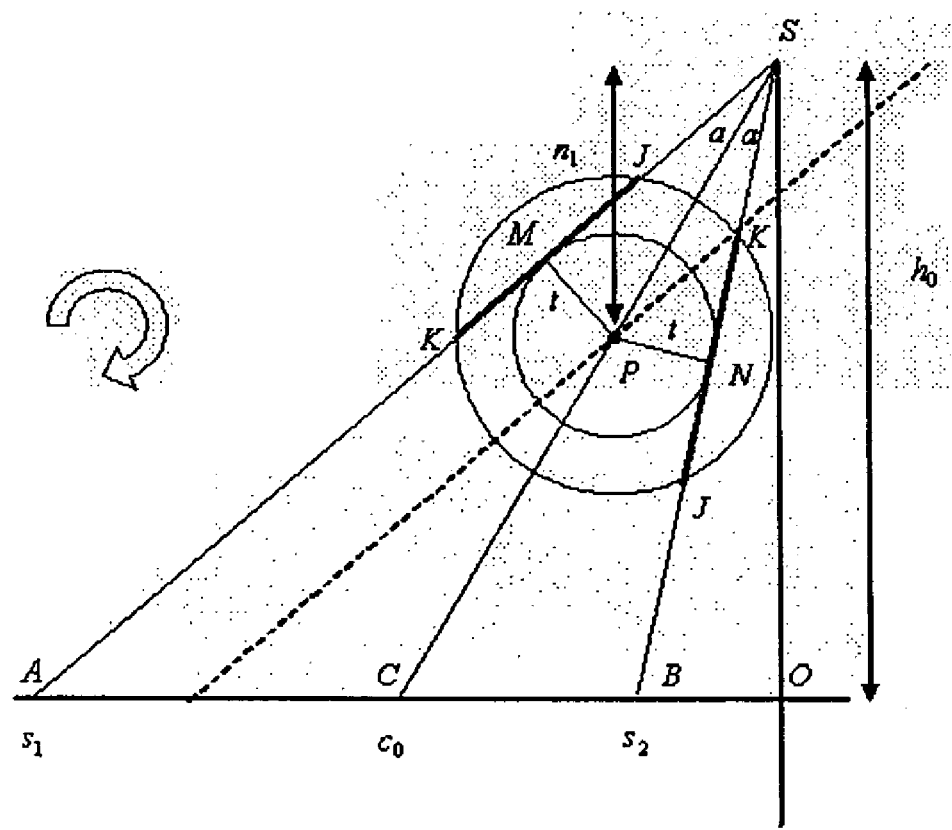
FIG. 7A illustrates the principle of an embodiment of the invention with a fan-beam system configuration with the two possible projection positions of one line on the object.

FIG. 7A illustrates the principle of an embodiment of the invention with a fan-beam configuration. With a fan-beam projection configuration, the object line JK is obtained by rotating the object line KJ an angle of ∠MPN. Actually, when the object is rotated over the rotation axis P, each line on the object only has two chances to align with the source point S. Suppose the two positions are $s_1$(KJ) at a scanning angle α and $s_2$ (JK) at the scanning angle α+β, β can be calculated as $$\beta(s_1) = \angle MPN \qquad (7)$$

$$= 180 - 2\angle ASC$$

$$= 180 - 2\left(\arctan\frac{s_1}{h_0} - \arctan\frac{c_0}{h_0}\right)$$

where $c_0$ is the true central ray and $h_0$ is the source-to-image distance (SID).

In this configuration, $s_2$ is also a function of $s_1$ $$s_2(s_1) = h_0 tg\angle BSO \qquad (8)$$

$$= h_0\left(2\arctan\frac{c_0}{h_0} - \arctan\frac{s_1}{h_0}\right)$$

Ignore the effect of the minor variation of the X-ray beam intensity over the detector pixels, we have $$P_\alpha(s_1) = P_{\alpha+\beta}(s_2) \qquad (9)$$

This property is the basis of our direct fan-beam central ray determination. We can assume a set of central ray values and perform the following measurement over each value $$M(c_i) = \sum_{\alpha=n_1}^{n_2} \sum_{s_1=t_1}^{t_2} [P_\alpha(s_1) - P_{\alpha+\beta(s_1)}(s_2(s_1))]^2 \qquad (10)$$

Obviously M should reach minimum when $c_i = c_0$.

Figure 8:
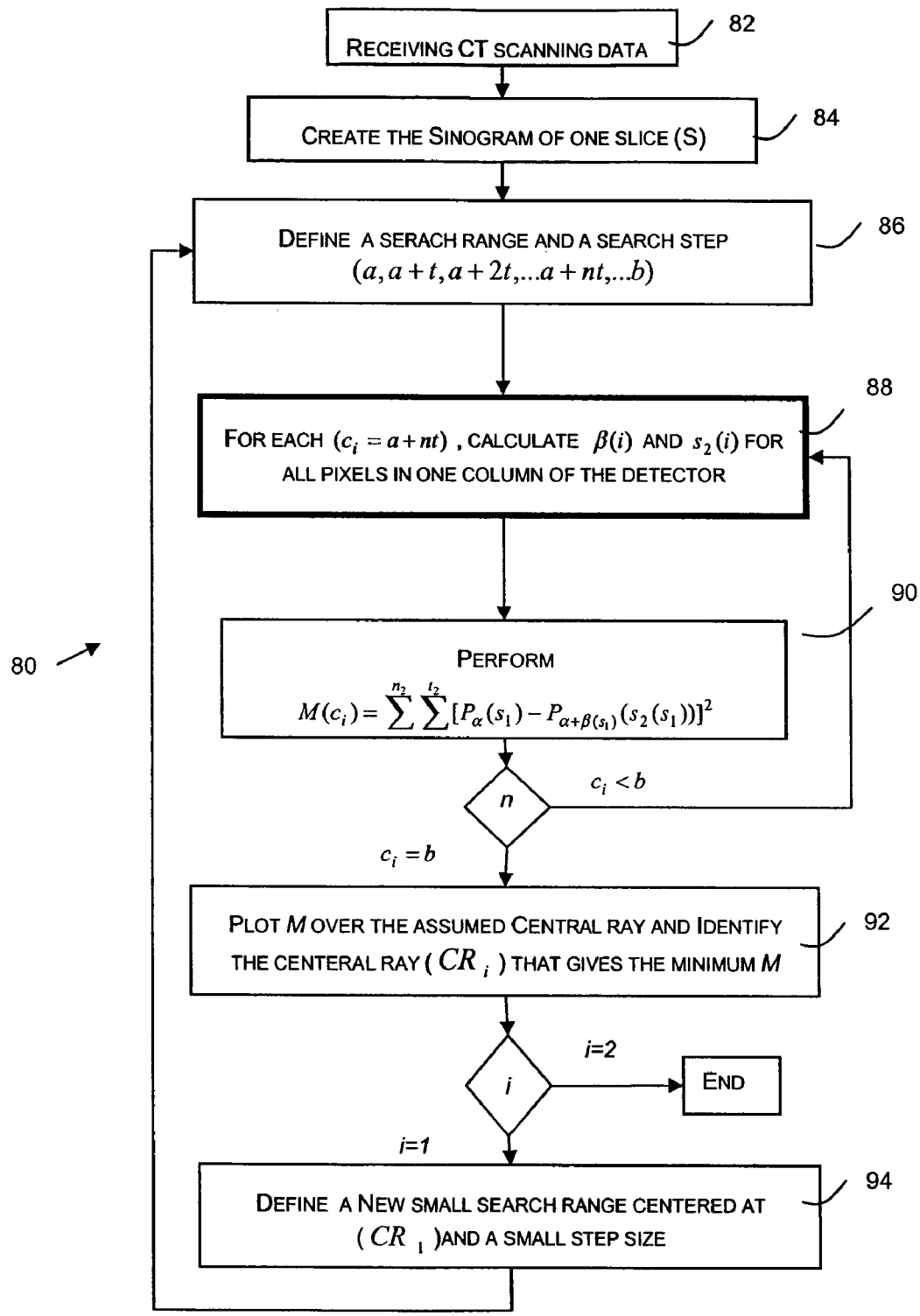
FIG. 8 is a flow chart for central ray determination in accordance with an embodiment of the invention.

FIG. 8 illustrates the flowchart of the first embodiment of the invention. After scanning an object 82, creating 84 a sinogram of one slice, defining a search range and a search step 86, calculating β(i) and $s_2$(i) for all pixels with an assumed central ray $c_i$ 88. Then perform a sum and square operation for all the pixels in the corresponding column within the range [t1, t2] (t1>=1, t2<=the number of pixels of the column) to the difference between the gray level at pixel i at projection angle α and the gray level at pixel at a projection angle α+β(i) over the projection angle range [n1, n2] (n1>=1, n2<=180 for a 360 degree scan with 1-degree angle increment.). The central ray value corresponding to the minimum of the measurement is identified as the best estimate to the real central ray that will be used for final CT reconstruction of the object.

It will be appreciated that a two-step or one-step search strategy can be considered. With a two-step strategy, the above process is first conducted 92 in a large search range with a large search step size. Then the central ray value is determined as the one corresponding to the minimum of the measurement and is used to define 94 the second search range with a small step size that is defined with the requirement for certain accuracy. The large search range in the first step is so defined that it will for sure include the true central ray value and make the search as short as possible. The small search step size is so defined that it will meet the requirement of the accuracy. In addition, the large search step size can be defined with a trade-off between the computation efficiency and the reliability of search. After the large step size is determined, the small search range can be generally defined as equal to or slightly greater than two times that of the large step size.

Figure 9:
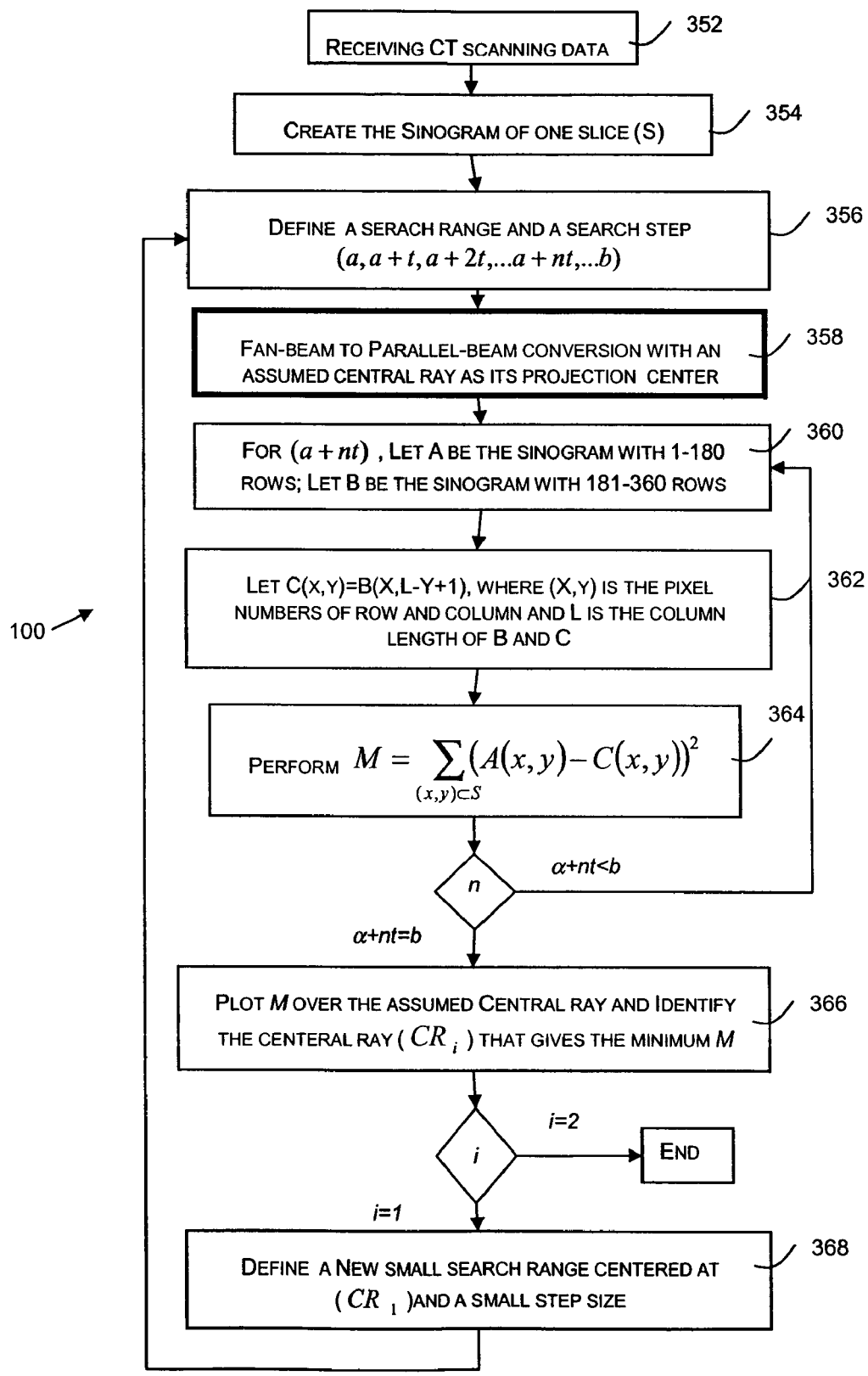
FIG. 9 is a flow chart for central ray determination in accordance with another embodiment of the invention.

FIG. 9 illustrates the flowchart of the second embodiment of the invention. After scanning an object 352, creating 354 a sinogram of one slice, and defining a search range and a search step 356, the fan-beam projection sinogram of one slice is converted 358 to parallel-beam sinogram with an assumed central ray as the projection centre.

Then the parallel-beam sinogram is separated 360 into part A and part B, part A being formed by 1-180 rows and part B by 181-360 rows. Part B is then flipped over the assumed central ray (the column centre) to become part C so that the last column in part B now becomes the first column in part C, the second column from the last in part B now becomes the second column in part C, etc. Then part A subtracts part C pixel by pixel to get part D. Part D is squared pixel by pixel to get part E. Sum the values of all pixels in part E to get a measurement of the mismatching level of part A and part C. Repeat this process over a set of assumed central ray values so that a relationship between the measurement and the assumed central ray values can be obtained. The central ray value corresponding to the minimum of the measurement is identified as the best estimate to the real central ray that will be used for final CT reconstruction of the object.

It will be appreciated that a two-step or one-step search strategy can be considered. With a two-step strategy, the above process is first conducted 366 in a large search range with a large search step size. Then the central ray value is determined as the one corresponding to the minimum of the measurement and is used to define 368 the second search range with a small step size that is defined with the requirement for certain accuracy. The large search range in the first step is so defined that it will for sure include the true central ray value. The small search step size is so defined that it will meet the requirement of the accuracy. In addition, the large search step size can be defined with a trade-off between the computation efficiency and the reliability of search. After the large step size is determined, the small search range can be generally defined as two times that of the large step size.

With a one-step strategy, the above process is conducted with a search range defined as the same as the large search range in above two-step strategy and with a step size defined as the same as the small step size in above two-step strategy.

Figure 10A:
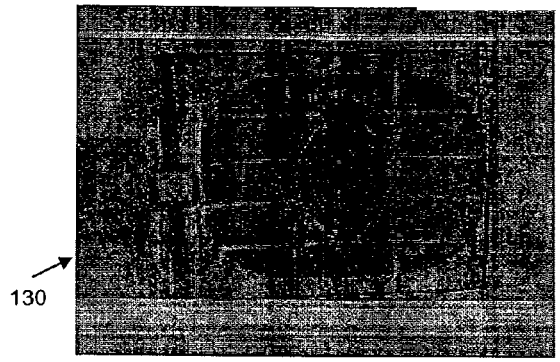
FIG. 10A-E shows a demonstration of an embodiment of the invention of an electronics cash card.
Figure 10B:
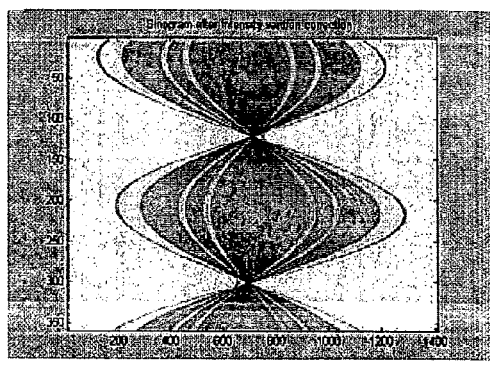
Figure 10C:
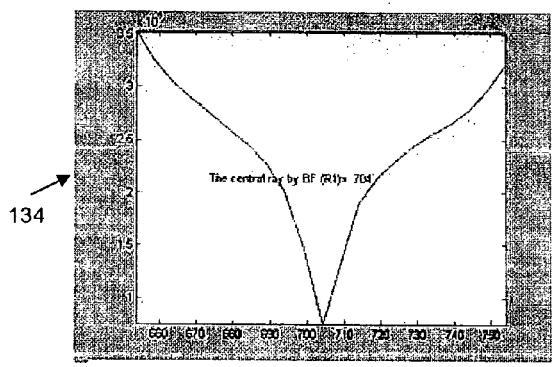
Figure 10D:
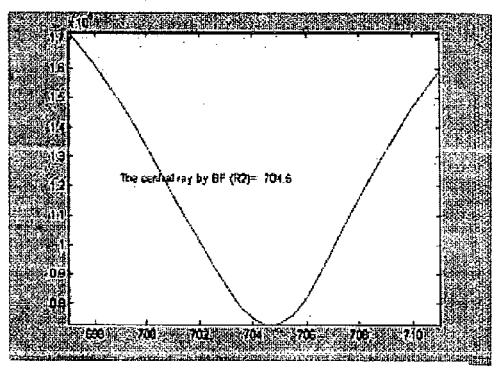
Figure 10E:
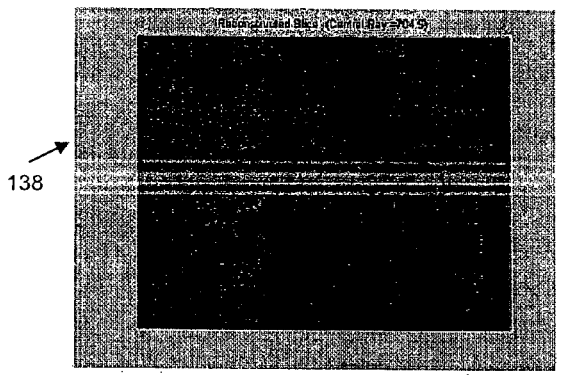

FIG. 10A-E is a demonstration of an embodiment of the invention with an electronic component on a cash card. FIG. 10A is a 2D view of the sample 130 of a cash card. FIG. 10B is the sinogram of one slice 132. FIG. 10C is the result of the rough search round 134. FIG. 10D is the result of the fine search round 136. FIG. 10E is the reconstructed image of the slice 138 with the central ray determined in FIG. 10D.

FIG. 11A-F shows the comparison for accuracy between an embodiment of the invention, the universal method and the wire phantom method. FIG. 11A is a 2D image of the wire phantom 180. FIG. 11B is a sinogram 180 of the wire phantom of FIG. 11A and the central ray determination in traditional way. The central ray determined by the wire phantom is 688.0798 as shown. FIG. 11C is a 2D image of a chip 184 which is scanned at the same position as the wire phantom. FIG. 11D is the sinogram of one slice of it 186. FIG. 11E is result of the fine search round 188 with the universal method. The central ray identified by this method is 687.9849. FIG. 11F is the result of the fine search round with an embodiment of the invention 189. The central ray determined in this way is also 687.9849. The three results of central ray agreed very well and the very small difference observed between the automated methods and the manual wire phantom method might come from the mechanical process required by mounting and dismounting the wire phantom and then mounting the object.

FIG. 12 shows a table 190 of the comparison for computation time between the universal central ray method and embodiments of the invention over different image sampling rates. For all these different data size processed, an embodiment of the invention only uses about $1/25^{th}$ the time required with universal method. However, comparing the results of the fine search round of the two methods they all give out stable determination of the central ray which is 687.9849.

Figure 13:
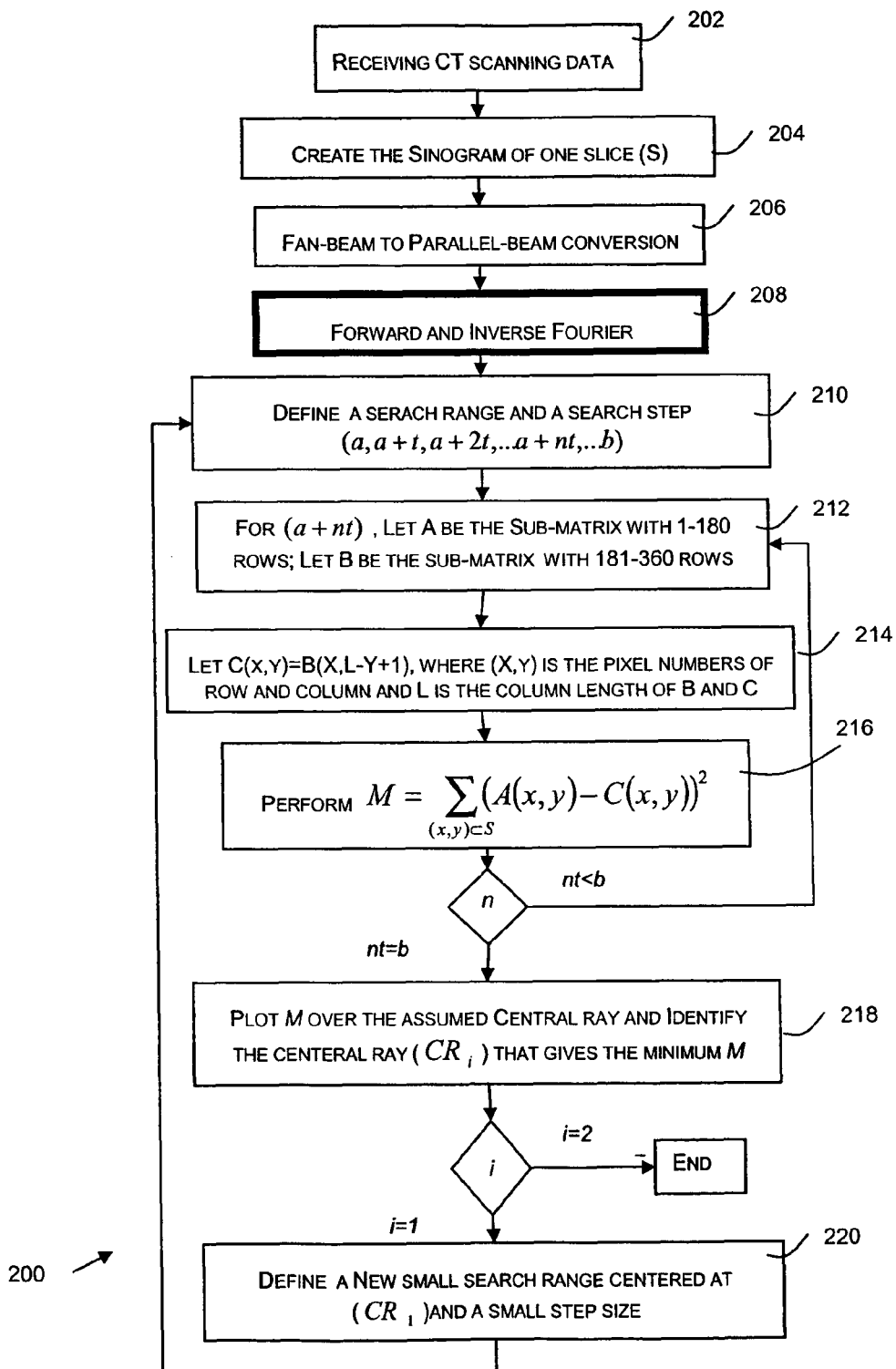
FIG. 13 is a flow chart of a method in accordance with an embodiment of the invention.

FIG. 13 shows the flow chart of an embodiment of the invention. Reference to the flow chart of FIG. 9 is made. Instead of using the projection data 360 after converting 358 the fan-beam projection to parallel-beam projection centred at a given central ray value, now the projection data after the forward and inverse Fourier transform processes 208 is used for the mismatching 210-214 level measurement over a set of assumed central ray, the remaining processes 202-204 and 212-220 correspond to 352-354 and 360-368, respectively. They are the same as the second embodiment of the invention as shown in FIG. 9.

Figures 14A, 14B:
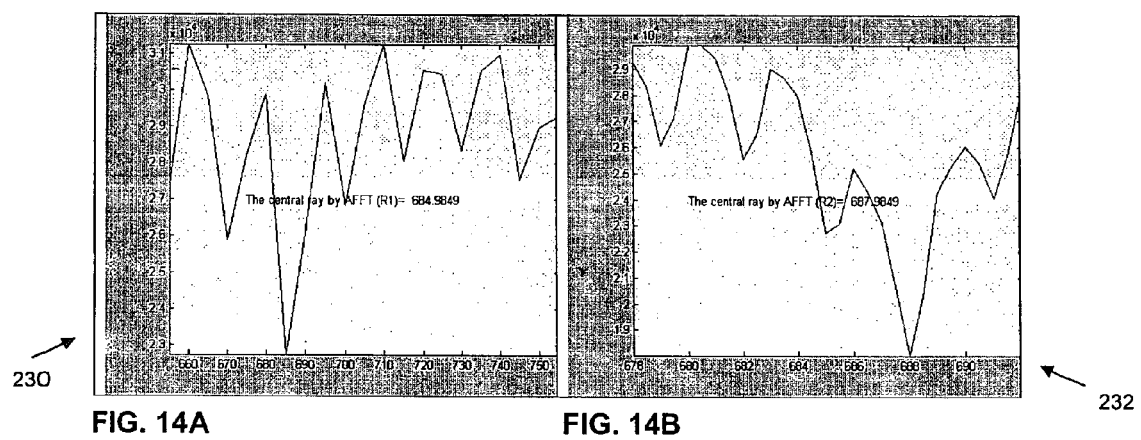
FIG. 14A-B shows the search results of a rough search round with a relatively large search range and large search step size (FIG. 14A) and a relatively fine search round with a small search range and a small step size (FIG. 14B) in accordance with an embodiment of the invention.

FIG. 14A-B shows the search result with this embodiment of the invention. FIG. 14A shows the result 230 of the rough search round and FIG. 14B shows the result 232 of the fine search round.

Figure 15:
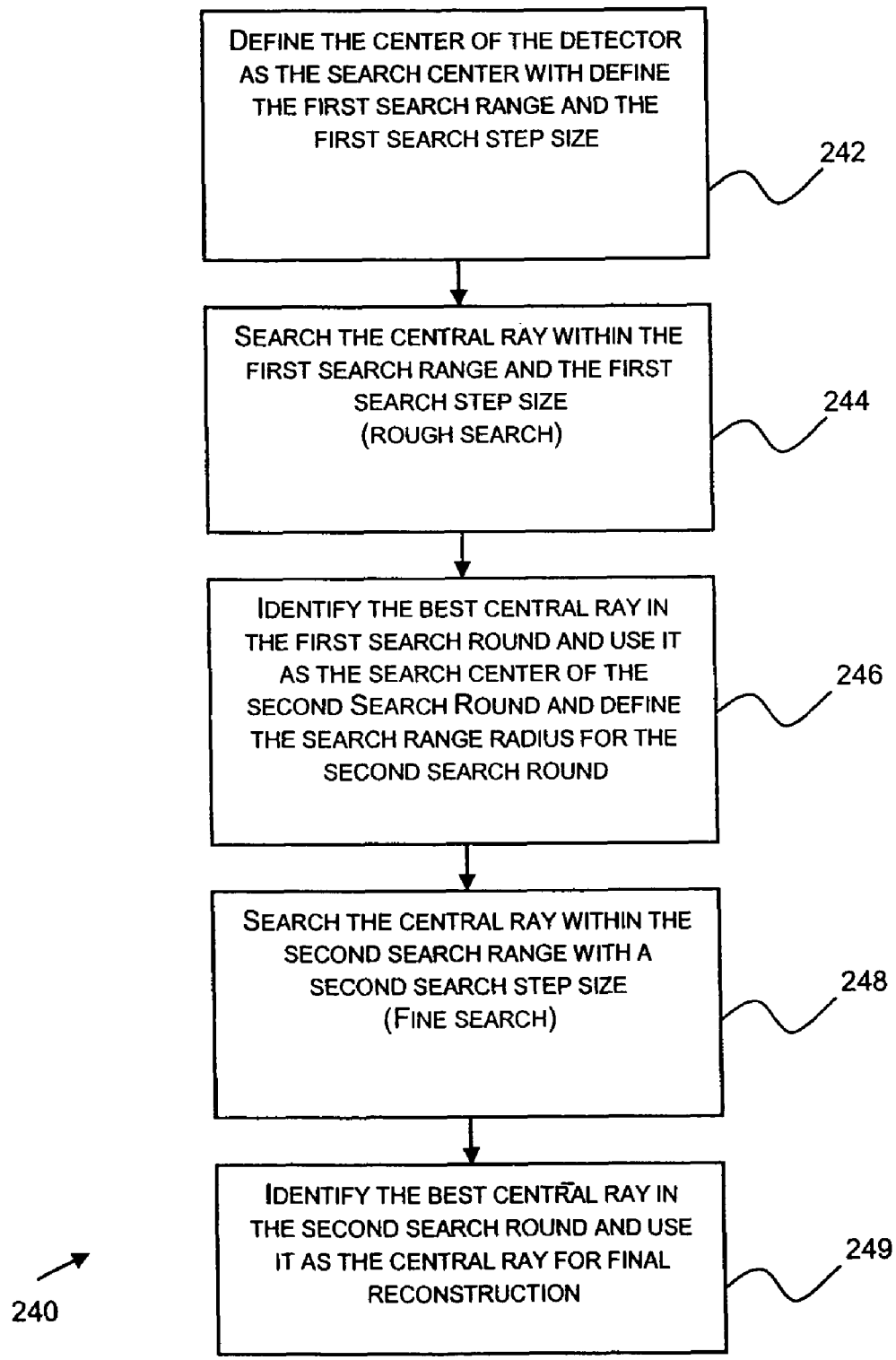
FIG. 15 is a flow chart of a method in accordance with an embodiment of the invention.

FIG. 15 shows a flow chart 240 of a method of an embodiment of the invention. The search central is first defined as the centre of the detector 242, with which a search radius is set for the rough search round 244. The remaining process 246-249 is the same with the first embodiment (FIG. 8) and the second embodiment (FIG. 9).

Figure 16:
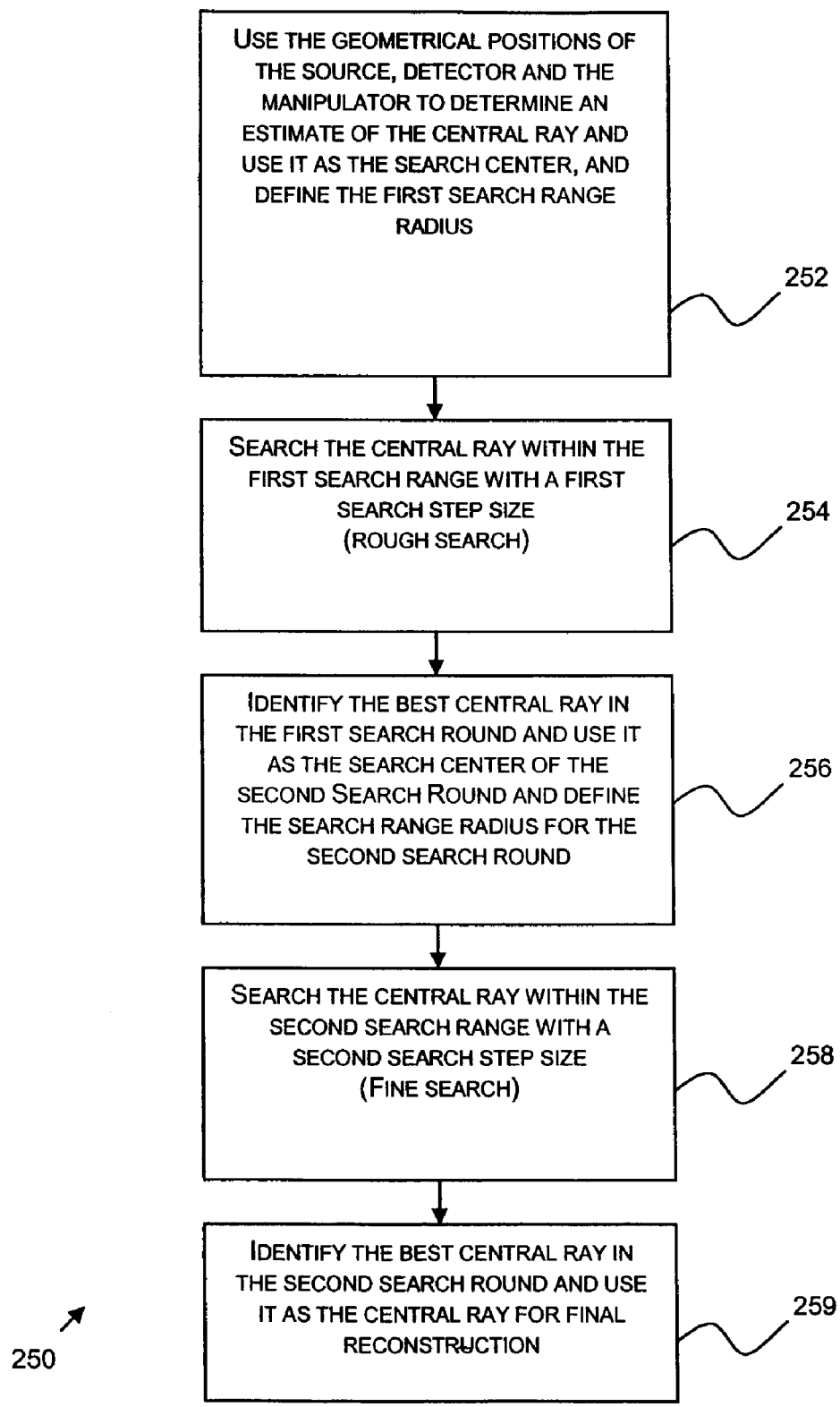
FIG. 16 is a flow chart of a method in accordance with an embodiment of the invention.

FIG. 16 shows a flow chart 250 of another embodiment of the invention. The search central is estimated first by using the geometrical relationship between the positions of the source 252, the detector and the rotary unit. A formula might be used to calculate 254 an estimate to the central ray, with which the search range for the first step search can be so defined that it is slightly lager than the uncertainty of the manipulator. The remaining process 256-259 is the same as the first embodiment (FIG. 8) and the second embodiment (FIG. 9).

FIG. 17A-D demonstrates the performance of embodiments of the invention with a normal scan. FIG. 17A is a 2D image of the sample 260. FIG. 17B is the sinogram of one slice 262. FIG. 17C is the result of the fine search round 264, obtained with a search range of 12 pixels and a search step size of 0.5 pixel. The search range and step size in the fine round are defined as 14 pixels and 0.5 pixel respectively. FIG. 17D is the reconstructed image of the slice 266.

Figure 18A:
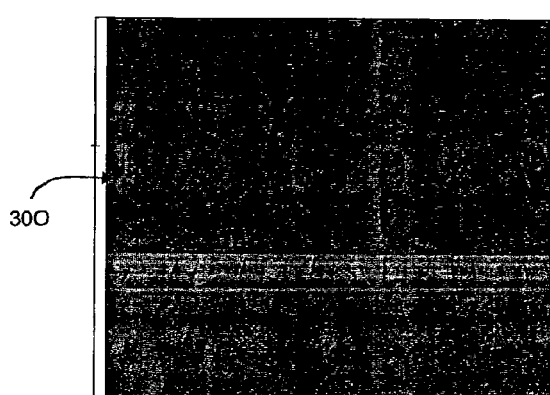
FIG. 18A-D demonstrates the performance of an embodiment of the invention of a high magnification scan.
Figure 18B:
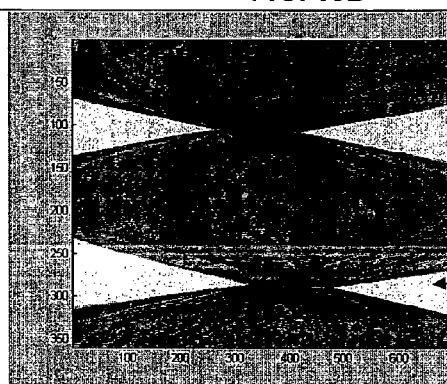
Figure 18C:
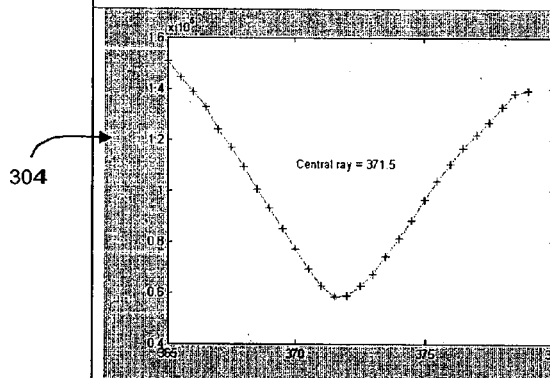
Figure 18D:
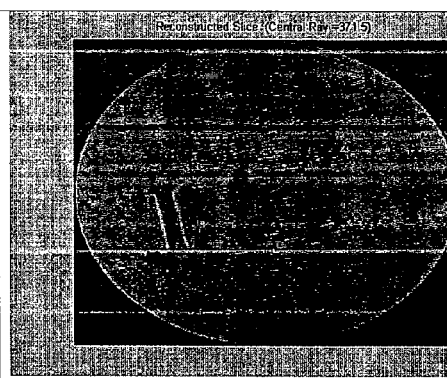

FIG. 18A-D demonstrates the performance of embodiments of the invention with a high-magnification scan. A high-magnification scan is such a scan that the object is put very close to the source to achieve higher resolution. For many cases, with such scan, the outer part of the object is possible to be outside the fan-beam 300,302 as shown in FIG. 18A and FIG. 18B. FIG. 18A is a 2D image 300 of the sample in FIG. 17k FIG. 18B is the sinogram of one slice 302. FIG. 18C shows that the central ray 304 can be identified without any ambiguity. FIG. 18D is the reconstructed image of the slice 306.

Figures 19A, 19B:
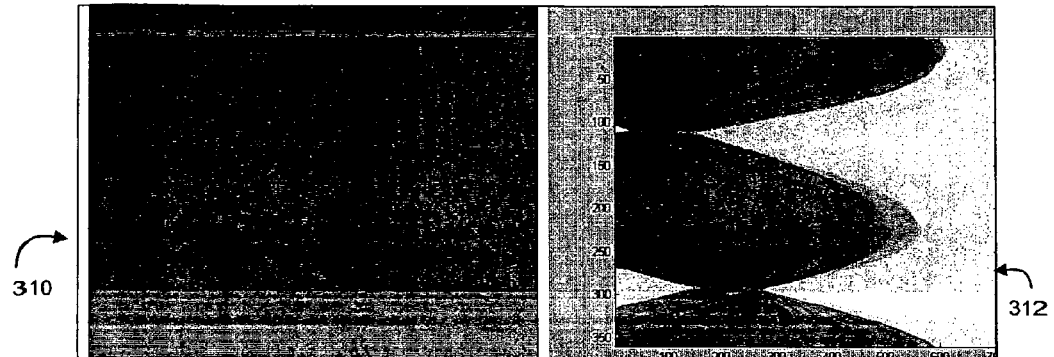
FIG. 19A-I demonstrates the performance of an embodiment of the invention of an offset scan.
Figures 19C, 19D:
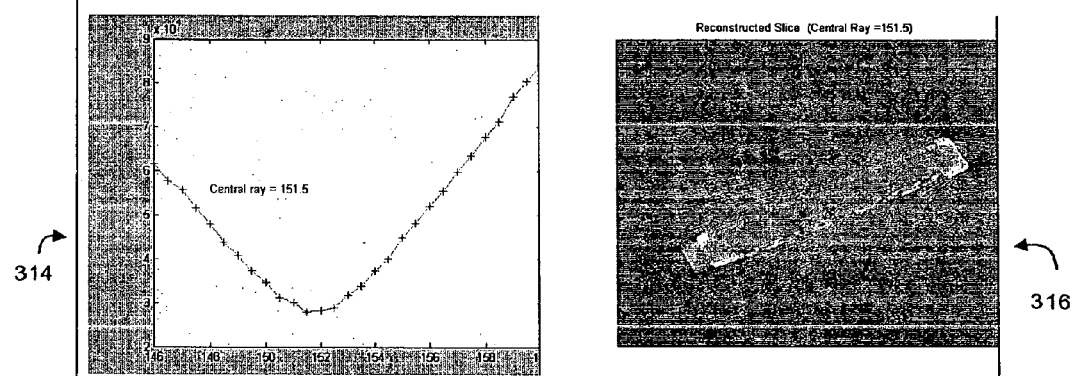
Figures 19E, 19F:
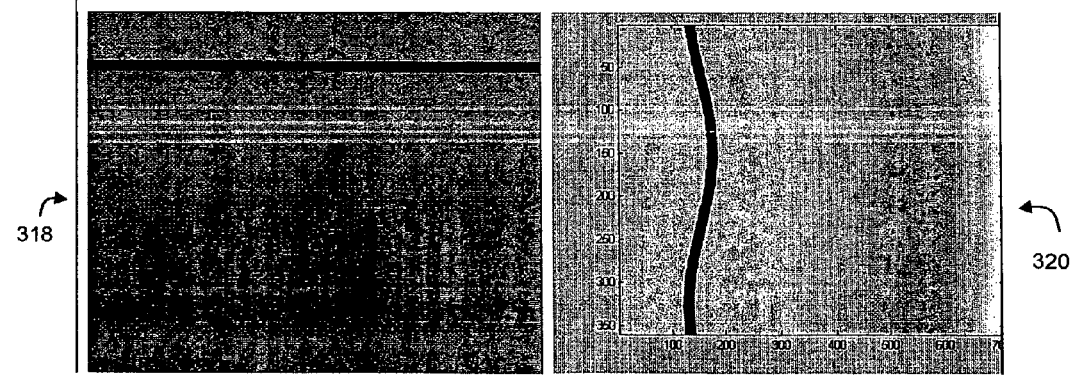
Figures 19G, 19H:
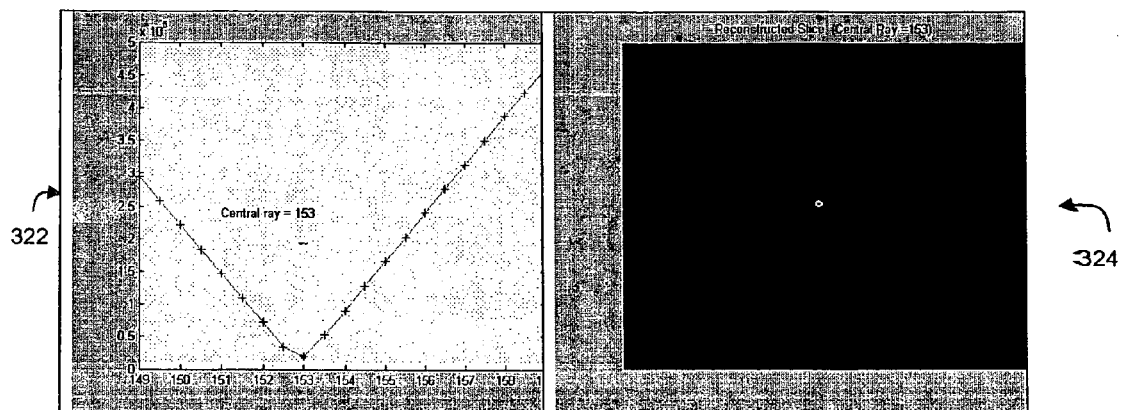
Figure 19I:
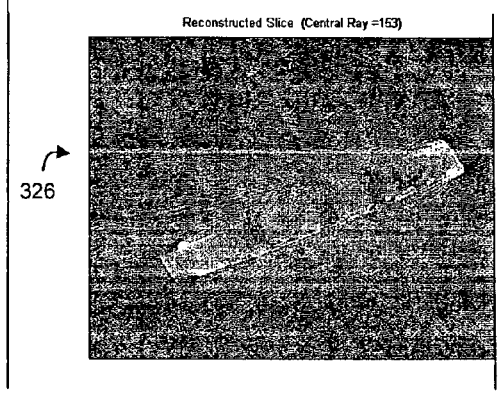

FIG. 19A-I demonstrates the performance of an embodiment of the invention for an offset scan. An offset scan is such scan that the object is put on one side of the detector so that either an almost doubled field-of-view can be obtained with a given magnification or an almost doubled magnification can be obtained with a given size of field of view. FIG. 19A is a 2D image of the same sample as in FIG. 17A 310. FIG. 19B is the sinogram 312 of one slice. FIG. 19C is the fine search result 314. FIG. 19D is the reconstructed image with the identified central ray 316. For comparison, a wire phantom is also scanned at the same position. FIG. 19E is a 2D image of the wire phantom 318, FIG. 19F is the corresponding sinogram 320. FIG. 19G is the fine search result 322. FIG. 19H is the reconstructed image 324 of the wire phantom slice. It will be appreciated that the central ray determined in this experiment by the wire phantom has a 1.5 pixel difference to that for the sample. To verify which one is more accurate, the same slice is reconstructed 316 as shown in FIG. 19D with the central ray value determined by the wire phantom. The result is shown in FIG. 19I, it is clear that its quality is not as good as that shown in FIG. 19D. The conclusion is that indeed embodiments of the invention accurately determines both the central ray of the wire phantom and the sample and the difference between them is possibly brought by the mechanical mounting and dismounting actions between scanning the sample and the wire phantom.

Advantageously, embodiments of the invention minimize the time required for central ray determination with the universal method. Therefore it still possesses the merits of the universal central ray determination method. Embodiments of the invention provide an automated central ray determination method directly using the projection data of the object to be inspected. Embodiments are compatible to work with all major scanning technologies such as normal scanning, high-magnification scanning and offset scanning. Embodiments of the invention are reliable and robust due to insensitivity to x-ray intensity variation and the poor contrast of the projection and provide accurate measurements of the reconstructed image quality without requiring additional scanning.

Additionally, when compared with the universal central ray method as shown in the table of FIG. 12, embodiments of the invention only take just $\frac{1}{25}^{th}$ the time that is required with the universal central ray method. Embodiments of the invention also require minimum amount of data storage and memory than that with the universal central ray method. In an embodiment, the central ray may be determined by just comparing the mismatching of the gray level of each pixel and the gray level of the calculated opposite projection pixel, obtained with a set of assumed central ray values. Both the sinogram data after the fan-beam to parallel-beam conversion and the data after the Forward Fourier transform and the inverse Fourier Transform can be used for the determination of central ray. Embodiments of the invention provide efficient central ray determination that has a good reliability and accuracy.

Embodiments of the invention are suitable for all CT systems that allow an adjustable centre of rotation. Additionally, it will be appreciated that embodiments of the invention may also be suitable for X-ray micro CT equipment makers for central ray determination and reconstructed image quality measurement.

It is to be understood that the embodiments, as described with respect to FIG. 5-19I, are for exemplary purposes, as many variations of the specific hardware used to implement the disclosed exemplary embodiments are possible. For example, the functionality of the devices and the subsystems of the embodiments may be implemented via one or more programmed computer system or devices. To implement such variations as well as other variations, a single computer system may be programmed to perform the functions of one or more of the devices and subsystems of the exemplary systems, the system having modules, for example of the processor or the like, for performing the process. For example, modules may be for selecting, calculating, measuring, identifying, estimating, or the like, the first projection pixel positions, second or opposite projection pixel positions, gray levels, projection angles, mismatch of gray levels, minimum measurements, or the like. On the other hand, two or more programmed computer systems or devices may be substituted for any one of the devices and subsystems of the exemplary systems. Accordingly, principles and advantages of distributed processing, such as redundancy, replication, and the like, also may be implemented, as desired, for example, to increase robustness and performance of the exemplary systems described with respect to FIG. 5-19I.

The exemplary systems described with respect to FIG. 5-19I may be used to store information relating to various processes described herein. This information may be stored in one or more memories, such as hard disk, optical disk, magneto-optical disk, RAM, and the like, of the devices and sub-systems of the embodiments. One or more databases of the devices and subsystems may store the information used to implement the exemplary embodiments. The databases may be organized using data structures, such as records, tables, arrays, fields, graphs, trees, lists, and the like, included in one or more memories, such as the memories listed above.

All or a portion of the exemplary systems described with respect to FIG. 5-19I may be conveniently implemented using one or more general-purpose computer systems, microprocessors, digital signal processors, micro-controllers, and the like, programmed according to the teachings of the disclosed exemplary embodiments. Appropriate software may be readily prepared by programmers of ordinary skill based on the teachings of the disclosed exemplary embodiments. In addition, the exemplary systems may be implemented by the preparation of application-specific integrated circuits or by interconnecting an appropriate network of component circuits.

While embodiments of the invention have been described and illustrated, it will be understood by those skilled in the technology concerned that many variations or modifications in details of design or construction may be made without departing from embodiments of the invention.

The invention claimed is:

1. A method for determining a true central ray of scanning an object placed between a fixed x-ray source and a detector in a computer tomography system, the method comprising:
    producing a beam of x-rays from the fixed x-ray source;
    detecting the x-rays at the detector;
    receiving scanning projection data comprising a plurality of pixels of the object under examination;
    rotating the object under examination using a manipulator;

selecting a first projection pixel position from the projection data, calculating a second projection pixel position, a gray level, and a projection angle for each pixel of the plurality of pixels for each one of a set of predetermined central rays;

measuring a mismatching of gray levels of each pixel of the plurality of pixels and its corresponding second projection pixel for each one of the set of predetermined central rays; and identifying the minimum of the measurement of the mismatching as an estimate of the true central ray;

wherein determining the first projection pixel position by defining a line formed with two points on the object, the line is aligned with the source and projected on the first projection pixel position;

wherein for each predetermined central ray, each line on the object has a first projection position and second projection position during a 360° scanning that is aligned with the source; wherein determining the second projection pixel position by determining the line aligned with the source during scanning; and wherein the second projection pixel position is calculated with a known source-to-detector distance.

2. A computed tomography system for determining a true central ray of scanning an object, the system comprising:
a fixed x-ray source configured to produce a beam;
a digital detector configured to detect an x-ray projection;
a manipulator configured to hold and rotate an object under examination in the beam; and
a processor configured to receive scanning projection data comprising a plurality of pixels of the object under examination from the digital detector;
wherein the processor further comprises a module configured to select a first projection pixel position from the projection data; calculate a second projection pixel position, a gray level, and a projection angle for each pixel of the plurality of pixels for each one of a set of predetermined central rays; measure a mismatching of gray levels of each pixel of the plurality of pixels and its corresponding second projection pixels for each one of the set of predetermined central rays; and identify the minimum of the measurement of the mismatching as an estimate of the true central ray;
wherein the processor is further configured to determine the first projection pixel position by defining a line formed with two points on the object, the line aligned with the source and projected on the first projection pixel position on the detector;
wherein for each predetermined central ray, each line on the object has a first projection position and second projection position during a 360° scanning that is aligned with the source;
wherein the processor is further configured to determine the second projection pixel position by determining the line aligned with the source during scanning; and
wherein the processor is further configured to calculate the second projection pixel position with a known source-to-detector distance.

3. The system of claim 2, wherein the processor is further configured to calculate for each predetermined central ray, the angle to rotate the object from the first projection position to the second projection position with a known source-to-detector distance.

4. The system of claim 2, wherein the processor is further configured to calculate the gray level of each pixel and corresponding second projection pixel position by performing a subtraction followed by a square/absolute followed by a sum over all pixels to get a measurement of the mismatching level of the pixels and their opposite projection pixels.

5. The system of claim 2, wherein the x-ray source is configured to produce at least one of a cone beam and a fan beam.

6. The system of claim 2, wherein the x-ray source produces a fan beam; and wherein the processor is further configured to convert fan-beam to parallel-beam projection and determine at least two sub-sinograms, measure the mismatching level of two sub-sinograms after a fan-beam to parallel-beam conversion with the set of predetermined central ray, and identify the minimum of the measurement of the mismatching as the estimate of the true central ray.

7. The system of claim 6, wherein the processor is further configured to form for each central ray in the set of predetermined central array, each of the two parallel-beam sub-sinograms with a row as a projection sequence number and a column as the pixels of the plurality of pixels.

8. The system of claim 7, wherein the processor is further configured to, for each assumed central ray one of the two sub-sinograms, perform a flip over its column corresponding to the assumed central ray to form a third sub-sinogram.

9. The system of claim 8, wherein the processor is further configured to perform, for the first and the third sub-sinograms, a pixel-wise subtraction followed by pixel-wise square/absolute followed by a sum over all pixels to get a measurement of the mismatching level of the two sub-sinograms.

10. The system of claim 2, wherein the processor is further configured to identify the central ray by measuring the mismatching level of gray levels by selecting a search range and a search step that are defined by each step corresponding to the minimum of the measurement.

11. The system of claim 2, wherein the processor is further configured to determine a rough search round with a first search range and a first search step size followed by a fine search round with a smaller second search range and a smaller search step.

12. The system of claim 11, wherein the processor is further configured to define the first search range by defining a search central and a search radius wherein the first search range is centered at the search central.

13. The system of claim 12, wherein the processor is further configured to define the search central of the first search range as the center of the detector for scans around a point proximate the central line of the detector.

14. The system of claim 12, wherein the processor is further configured to define the search central of the first search range from the geometrical relationship between the positions of the source, the detector and the manipulator for a particular scanning.

15. The system of claim 6, wherein the processor is further configured to determine the central ray with the scanning projection data of the object under examination by measuring the mismatching level of two sub-matrices of projection data after the forward Fourier transform and inverse Fourier transform.

16. The system of claim 15, wherein the processor is further configured to form for each assumed central ray, each of the two sub-matrices with a row as a projection sequence number and a column as the pixels of the plurality of pixels.

17. The system of claim 15, wherein the processor is further configured to perform for each assumed central ray, for one of the two sub-matrix a flip over its column corresponding to the assumed central ray to form a third sub-matrix.

18. The system of claim 17, wherein the processor is further configured to perform, for the first and the third sub-matrix, a pixel-wise subtraction followed by pixel-wise square/absolute followed by a sum over all pixels to get a measurement of the mismatching level of the two sub-matrices.

19. The system of claim 15, wherein the processor is further configured to define a search range and a search step with each predetermined central ray in the search range, measure the mismatching level, and identify the true central ray as the central ray value corresponding to the minimum of the measurement.

* * * * *